United States Patent [19]

Moberg et al.

[11] Patent Number: 5,230,704
[45] Date of Patent: Jul. 27, 1993

[54] SUCTION/IRRIGATION INSTRUMENT HAVING REUSABLE HANDLE WITH DISPOSABLE FLUID PATH

[75] Inventors: John R. Moberg, Lakeville; Joseph A. Marino; Matthew E. Bellin, both of Apple Valley, all of Minn.

[73] Assignee: Biomedical Dynamics Corporation, Burnsville, Minn.

[21] Appl. No.: 904,720

[22] Filed: Jun. 26, 1992

[51] Int. Cl.⁵ .............................................. A61M 1/00
[52] U.S. Cl. .................................... 604/34; 604/35; 604/250; 604/902
[58] Field of Search ............... 604/19, 27, 30, 33–35, 604/39, 43, 250, 275, 902

[56] References Cited

U.S. PATENT DOCUMENTS

| | | |
|---|---|---|
| 3,438,607 | 4/1969 | Williams et al. . |
| 3,825,004 | 7/1974 | Durden, III ........................ 604/902 |
| 3,889,675 | 6/1975 | Stewart . |
| 4,299,221 | 11/1981 | Phillips et al. ...................... 604/30 |
| 4,460,358 | 7/1984 | Somerville et al. . |
| 4,519,385 | 5/1985 | Atkinson et al. ................... 604/27 |
| 4,526,573 | 7/1985 | Lester et al. ........................ 604/33 |
| 4,617,013 | 10/1986 | Betz .................................... 604/902 |
| 4,628,940 | 12/1986 | Näslund . |
| 4,662,871 | 5/1987 | Rafelson ............................ 604/902 |
| 4,696,669 | 9/1987 | Menhusen .......................... 604/275 |
| 4,708,717 | 11/1987 | Deane et al. ....................... 604/43 |
| 4,713,051 | 12/1987 | Steppe et al. . |
| 4,731,052 | 3/1988 | Seitz, Jr. . |
| 4,798,580 | 1/1989 | DeMeo et al. . |
| 4,852,551 | 8/1989 | Opie et al. . |
| 4,941,872 | 7/1990 | Felix et al. ......................... 604/27 |
| 4,964,849 | 10/1990 | Robicsek ............................ 604/902 |
| 4,982,739 | 1/1991 | Hemstreet et al. . |
| 5,147,292 | 9/1992 | Kullas et al. ....................... 604/34 |
| 5,186,714 | 2/1993 | Boudreault et al. ............... 604/35 |

FOREIGN PATENT DOCUMENTS

| | | |
|---|---|---|
| 0303557 | 2/1989 | European Pat. Off. ........... 604/35 |
| 1101702 | 3/1961 | Fed. Rep. of Germany ...... 604/34 |
| 1903367 | 8/1970 | Fed. Rep. of Germany ...... 604/35 |

Primary Examiner—Ralph Lewis
Attorney, Agent, or Firm—Haugen and Nikolai

[57] ABSTRACT

A suction/irrigator surgical instrument comprises a replaceable cartridge containing the entirety of the fluid flow path for the instrument and a reusable flow-control member having trigger-actuated levers for selectively opening and occluding a portion of the fluid flow path when the two members are affixed to one another, in piggy-back fashion, to form a pistol-grip for the instrument.

17 Claims, 2 Drawing Sheets

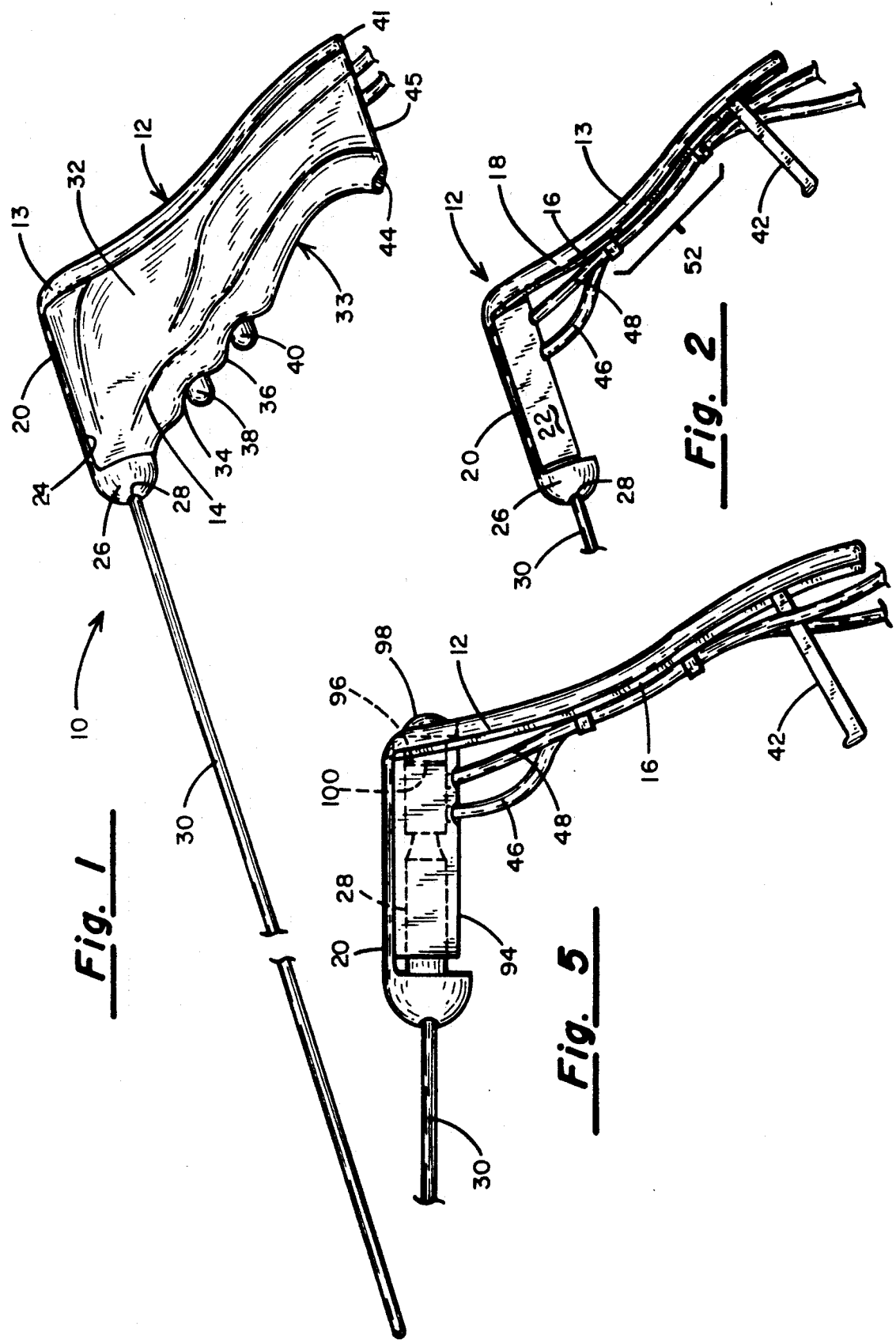

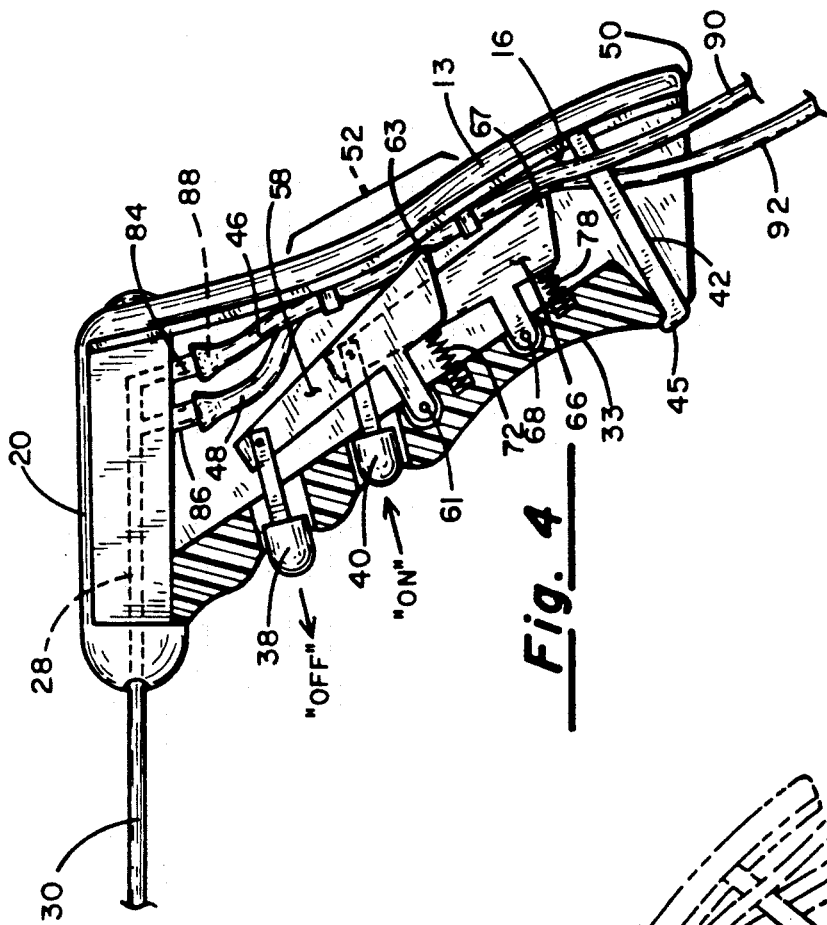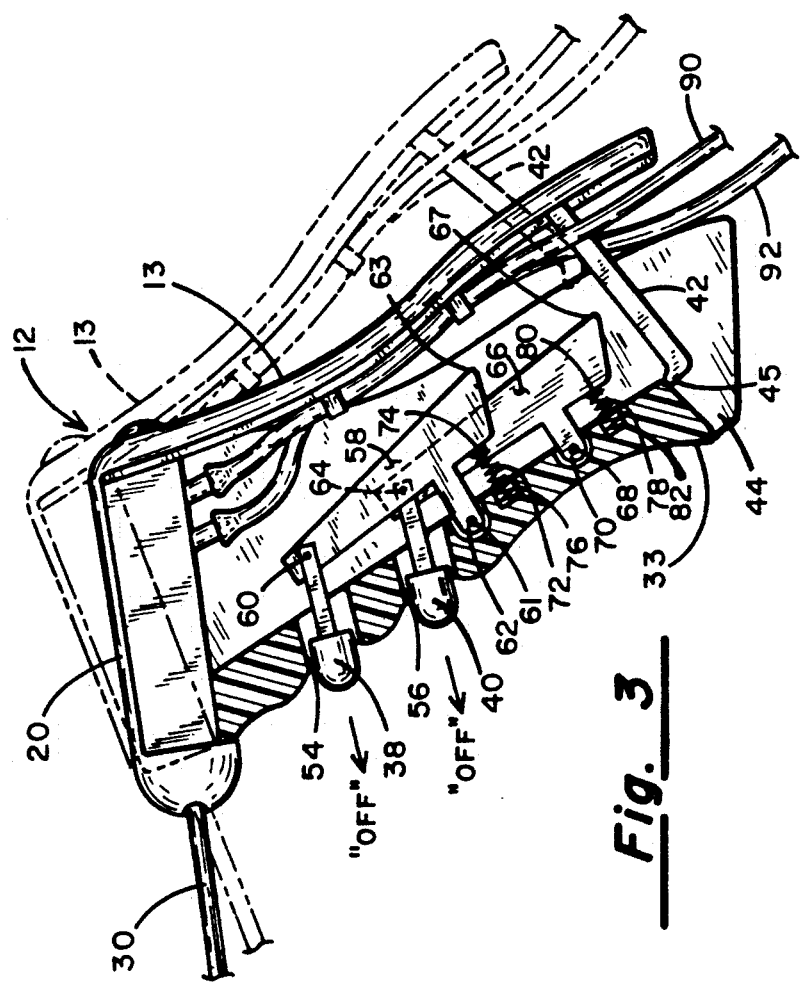

SUCTION/IRRIGATION INSTRUMENT HAVING REUSABLE HANDLE WITH DISPOSABLE FLUID PATH

BACKGROUND OF THE INVENTION

I. FIELD OF THE INVENTION

This invention relates generally to a surgical instrument for selectively irrigating and aspirating fluids during the course of a surgical procedure, and more particularly such an instrument which is readily suitable for use in endoscopic procedures. It is particularly characterized in that the fluid conveying portions of the instrument are disposable while the flow control elements thereof are reusable.

II. DISCUSSION OF THE PRIOR ART

When conducting minimally invasive surgical procedures, such as abdominal surgery using laparoscopic procedures, rather than creating a large incision, three or four small puncture wounds are formed through the abdominal wall which permit a series of cannulae to be inserted therethrough. One cannula will accommodate an endoscope (laparoscope) allowing the internal surgical site to be illuminated and the scene displayed on a video screen. Another cannula may typically provide for the introduction of special surgical instruments for dissecting and excising tissue while yet another cannula accommodates an instrument for grasping and manipulating the origin or other tissue to be excised.

While the use of laser-based instruments or electrosurgical instruments can be used to effect coagulation of blood seeping from severed blood vessels, it frequently becomes necessary during the course of an endoscopic procedure to irrigate within the body cavity to remove blood and other body fluids which may obstruct the view being presented to the surgeon. On an as needed basis, a suction/irrigator may have a portion thereof passed through a cannula and then, by manipulating appropriate flow control devices, a liquid, such as saline, can be used to flush the surgical site. Subsequently, a vacuum may be applied to aspirate the saline and other body fluids to restore the view of the surgical field and the tissue being excised as the surgical procedure takes place.

A typical prior art suction/irrigator for endoscopic use includes an elongated rigid tube which is adapted to be passed through the lumen of a cannula and which is adapted to be coupled to a supply of flushing liquid and/or to a vacuum source, via one or more flow control valves. Typical of such a prior art suction/irrigator instrument is that sold by the Cabot Company of Langhorne, PA. The flow control valves in that reusable device are similar to trumpet valves, whereby depression of one or the other of a pair of spring loaded push buttons allows either the flushing liquid to pass down the rigid tubular portion of the instrument into the surgical site or, alternatively, allows blood and other body fluids to be drawn from the surgical site through the rigid tube and the flow control valves to a collection vessel coupled to a source of vacuum. Because the fluids flow through the trumpet valves, when it comes time to clean and sterilize the instrument following a first surgery to make it ready for a subsequent procedure with a different patient, the valve and valve housing must be disassembled for cleaning and sterilization and then later reassembled and relubricated. Because it is difficult to get access to all of the surfaces that may come in contact with body fluids, it makes it difficult to clean and sterilize for reuse. Also, because of the materials selected and complexity of the valving system, the instrument tends to be too costly to be considered "single-use" or "disposable".

The Storz suction/irrigation probe manufactured by Wisap of West Germany is partially a reusable device utilizing a pinch valve to control the fluid flow through a tube. In this device, only a part of a fluid path is disposed of after use. The instrument's elongated rigid tube designed to pass through a cannula must be manually cleaned with pipe cleaners etc. and the entire reusable unit must be rinsed and/or autoclaved. Still another prior art suction/irrigator is a totally disposable unit also made and sold by Cabot. While this suction/irrigator probe has been manufactured at a sufficiently low cost so as to be considered entirely disposable, the cost reduction has been accomplished with sacrifice in quality, ease of handling and other ergonomic considerations. Moreover, its cost necessarily exceeds the cost of the present invention for reasons that will become apparent as the description thereof proceeds.

It is accordingly a principle object of the invention to provide a suction/irrigator surgical instrument in which the entire fluid path of the instrument is designed to be disposable, but where the higher cost flow control members contained within a handle-like housing are reusable and designed to be readily cleaned and sterilized for subsequent use with a simple, low-cost replacement cartridge containing the instrument's fluid path.

SUMMARY OF THE INVENTION

In accordance with the present invention, there is provided a suction/irrigator surgical instrument which comprises a disposable cartridge and a reusable, flow-control member. The cartridge includes a back up member having first and second ends. Integrally formed at the first end is a tubular barrel and located near the second end is a latch element. An elongated, generally rigid tube extends distally from the tubular barrel and at least one flexible, compressible tube made from a natural or polymeric material extends between the first and second ends of the backup member so as to abut the backup member over a predetermined zone. This compressible tube or tubes is/are coupled in fluid communication with the rigid tube.

The reusable, flow control member comprises a housing having a recess or channel in a top surface thereof for receiving and supporting the tubular barrel of the disposable cartridge. At least one spring biased lever is pivotally supported within the housing, with one end of the lever comprising a trigger which is manually assessable through an aperture formed in the housing. The working end of the lever normally pinches the flexible tube against the backup member in the zone with sufficient force to occlude the lumen of the flexible tube. The housing further incorporates a mating latch element for receiving the latch element of the disposable cartridge and thereby holding the cartridge to the flow control member in a piggy-back fashion. Because the fluids used during irrigation and subsequent aspiration do not come in contact with the spring biased levers within the interior of the housing, significantly less cleaning is required to make the housing ready for subsequent use with a sterile replacement cartridge.

Unlike the Storz-Wisap, the Cabot Corson and the Cabot reusable suction/irrigation instruments, the housing of the present invention is ergonomically contoured to conform to the surgeon's hand to provide a comfortable pistol-like grip with the trigger portion of the flow control levers conveniently accessible for finger-tip actuation.

DESCRIPTION OF THE DRAWINGS

The foregoing features, objects and advantages of the invention will become apparent to those skilled in the art from the following detailed description of the preferred embodiment, especially when considering in conjunction with the accompanying drawings in which:

FIG. 1 is a perspective view of the suction/irrigator surgical instrument of the present invention;

FIG. 2 is a perspective view of the replaceable cartridge portion of the suction/irrigator instrument of FIG. 1;

FIG. 3 is a side, partially crossed sectioned view showing the interior of the reusable, flow-control member and the manner in which the replaceable cartridge is installed.

FIG. 4 is a side, partially sectioned view of the suction/irrigator surgical instrument of Figure with the replaceable cartridge operatively joined to the reusable flow control housing member; and FIG. 5 illustrates an alternative design of the replaceable cartridge.

DESCRIPTION OF THE PREFERRED EMBODIMENT

Referring to FIGS. 1 and 2, there is indicated generally by numeral 10 a suction/irrigator surgical instrument in accordance with the present invention. It is seen to include a disposable cartridge member 12 which is coupled to a reusable, flow-control member 14. As can best be seen in FIG. 2, the disposable cartridge 12 comprises a backup member 13 preferably having a smooth arcuate outer contour to conform to the hand and a generally flat interior surface 16. Projecting outwardly from the surface 16 proximate the upper end 18 of the backup member 13 is a integrally molded tubular barrel 20 which flattened on opposed sides, as at 22 (FIG. 2), so as to fit within a mating channel or recess formed in the top surface 24 of the reusable flow control member 14. The distal end 26 of the integrally molded barrel segment 20 is generally hemispherically shaped and a longitudinal bore 28 extends through the length of the barrel 20, as will be more fully disclosed hereinbelow. Fitted into the bore 28 in the barrel and extending outward therefrom is a relatively long, generally rigid tube 30. It is preferably formed from either stainless steel or a suitable, medical-grade plastic and has an outside diameter sufficiently small so that it can be passed through the lumen of a cannula of the type commonly used in endoscopic surgery.

The reusable, flow-control member 14 and the cartridge member 12 are smoothly contoured so as to form a pistol-like grip having a slight indentation in the area identified by numeral 32 for comfortably receiving the surgeons thumb. On its forward or distal facing edge 33 are first and second step-like notches 34 and 36 having apertures therein from which project rounded trigger members 38 and 40. When the grip is held in the hand with the thumb in the recess area 32, typically the forefinger and middle finger can be used to selectively depress either the trigger 38 or the trigger 40, depending upon whether irrigation or aspiration is to be effected.

With reference again to FIG. 2, it can be seen that extending from the lower or butt end 41 of the backup member 14 is a latch element 42 which is designed to cooperate with a mating latch element 44 formed on the butt end 45 of the housing 14. As will be explained further hereinbelow, when the replaceable cartridge 12 is being mated with the flow-control member housing 14 the latch 42 snaps into the recess 44 to retain these parts secured to one another. When it is desired to remove the replaceable cartridge, the latch 42 is manually depressed until the two are released, allowing the backup member 13 to be swung away from the rear or proximal surface of the housing member 14. FIG. 2 also shows a pair of flexible, compressible tubes 46 and 48. These tubes each have a lumen in fluid communication with the bore 28 formed longitudinally in the barrel 20. The tubes 46 and 48 are routed toward the butt end 41 of the backup member 13 and in a zone indicated generally by the bracket 52, the tubes 46 and 48 are arranged to rest against the flat surface 16 of the backup member 13.

FIG. 3 is a partially sectioned view of the instrument of FIG. 1 showing the internal parts contained within the reusable, flow control member 14. Formed inward in the proximal face 33 of the housing are first and second apertures 54 and 56 through which the trigger members 38 and 40 project. Trigger member 38 is pivotally joined to a first lever 58 at a pivot point 60. The lever 58 is, in turn, pivotally joined to the front face 33 of the housing by a pin 61 which passes through an ear 62 projecting from a forward edge of the lever 58. Likewise, the trigger 40 is pivotally joined at 64 to a lever 66 which, in turn, is pivotally jointed to the housing by a pin 68 extending through an integrally formed ear 70 which projects laterally from the lever 66.

A first compression spring 72 is constrained between a cylindrical boss 74 formed on the lever 58 and a cylindrical recess 76 formed in the face 33 of the housing. It normally biases the lever 58 so that its trigger member 38 extends outward through the opening 54. In a similar fashion, a compression spring 78 surrounds a cylindrical boss 80 formed on the lever 66 and its other end resides in a mating recess 82 formed in the inner wall of the housing face 32. The compression spring 78 also normally urges the lever 66 such that its trigger member 40 projects outward through the opening 56.

FIG. 3 is useful in illustrating the manner in which the disposable cartridge 12 can be attached to and removed from the housing comprising the reusable flow-control member 14. In assembling the parts together, the hemispherical end portion 26 of the cartridge 12 is positioned in front of the U-shaped groove formed in the upper end of the housing with the backup member 13 inclined in the position represented by the phantom line presentation. The backup member is then manually pressed against the proximal end of the housing until the latch member 42 passes through the latch opening 44 allowing the barb 45 to engage the outer surface 32 of the housing.

FIG. 4 also illustrates one way in which the upper ends of the flexible, compressible tubes 46 and 48 may be coupled to the lumen defined by the bore 28 in the barrel member 20. Specifically, barbed tubular stubs 84 and 86 may be integrally molded with the barrel 20 and each of the stubs has a lumen intersecting the bore 28. The tubing members 46 and 48, preferably formed of silicone rubber, latex or polyvinyl chloride, have their ends forced over the barbs 88 of stubs 84 and 86. The opposite or lower ends 90 and 92 of the flexible deformable tubes 46 and 48 are adapted to be coupled, one to a source of liquid under pressure and the other to a vacuum source via an appropriate coupler such as a luer fitting (not shown).

With reference to FIG. 5, there is shown an alternative way of configuring the flexible tubes 46 and 48 for attachment to the lumen of the rigid tubular member 30. As can be seen from this drawing, the rigid tube 30 has its proximal end extending completely through a bore 28 formed in the barrel member 20 so that the end thereof can fit into a tubular sleeve 94 which is integrally molded onto the upper ends of the flexible tubes 46 and 48. The backup member 12 may be provided with an opening as at 96 which adapted to receive a mating plug 98 which can be removed, if desired, to provide access to the lumen of the sleeve 94. This permits another surgical instrument, such as a scissors, an electrosurgical scalpel, etc., to be passed down the lumen of the rigid tube 30, during the course of a surgical procedure. A seal 100 is integrally disposed within the lumen of the sleeve 94 proximal of the union of the flexible, compressible tubes 46 and 48 with the sleeve 94. This seal is preferably an elastomeric disc having an opening formed through it. The opening is of a size which permits an instrument to be inserted through the seal member 100 with the seal then conforming to the exterior dimension of that instrument to block the flow of liquid or the escape of an insufflating gas via the bore 96.

OPERATION

The disposable cartridge portion of the suction/irrigator instrument shown in FIGS. 2 and 5 typically will be removed from a sterile package in the operating room and will be joined to a sterile, reusable, flow-control member 14 in the manner illustrated in FIG. 3. That is, the nose portion 26 of the tubular barrel 20 is fitted in front of the channel formed in the upper edge 24 of the housing with the backup member 13 being positioned at an angle to the rear edge of the housing. Then, by swinging the lower end of the backup member 13 toward the housing, the latch member 42 is made to pass through the latch opening 44 in the housing until the barb 45 engages the front face of the housing.

When the two members are latched, one to the other, the lower most ends 63 and 67 of the levers 58 and 66 squeeze the tubes 46 and 48 against the surface 16 of the backup member in the zone indicated by bracket 52 and thereby occlude the lumens of the those tubes, preventing fluid flow therethrough. In the view of FIG. 4, the spring 72 is shown as compressing the end 63 of lever 58 into the tube 46 to thereby occlude its lumen. The trigger 40 associated with lever 66 is illustrated in its depressed position in which the lever 66 has been rotated about its pivot point 68 to thereby compress the spring 78 and disengage the end 67 of the lever from pinching or squeezing the tube 48. Fluid is no longer blocked from flowing through that tube.

Assuming that a source of irrigation liquid, such as saline under pressure, is coupled to the end 92 of the tube 48 when the trigger 40 is depressed, the irrigation liquid will flow through tube 48, through the barrel 20 and the rigid tube 30 to irrigate a surgical site within a patient. The surgeon, by removing his finger form trigger 30, will allow the spring 78 to again move the lever into a position where its end 67 squeezes and occludes the tube. By next pressing trigger 38, the lever 58 is lifted relative to the tube 46. Assuming that a vacuum source has been coupled to the end 90 of the tube 46, body fluids and irrigation liquids will be drawn through the rigid tube 30, the barrel 20, and the flexible tube 46 to a collection chamber associated with the vacuum source.

It is worthy of note that the fulcrums 61 and 68 for the levers 58 and 66, respectively, are located a greater distance from their associated trigger members 38 and 40 than they are from the load point at which the springs 72 and 78 are positioned. As such, less finger force is required to compress the springs 72 and 78 because of the mechanical advantage afforded by the levers. The springs 72 and 78 are of course, designed to provide sufficient force to squeeze the tubes 46 and 48 closed against the back-up member 13. By selectively manipulating either one of the triggers 38 or 40, irrigation liquid may be made to flow through the instrument to the surgical site and suction may be created to draw body fluids and irrigation liquid back through the rigid tube and the flexible tube coupled to the vacuum source.

With reference to FIG. 5, by removing the fitted cap or plug 98 from the cartridge, access can be gained to the lumen of the plastic tubular sleeve 94 and the lumen of the tube 30. Accordingly, another endoscopic surgical instrument can be inserted through the rigid tube when desired. The elastomeric seal 100 with its negative clearance opening precludes any insufflation gas from escaping through the instrument and also provides an effective seal around any instrument that may be inserted through the bore 96 in the barrel 20 and through the lumen of the sleeve 94.

While there has been shown and described a preferred embodiment of the invention, those skilled in the art will realize that various changes and modifications may be made to it and therefore, the disclosed embodiment should not be considered as limiting the invention, the scope of the invention being determined by the following claims.

We claim:

1. A suction/irrigator surgical instrument, comprising:
   (a) a disposable cartridge including:
      (i) a back-up member having first and second ends with an integrally formed tubular barrel at said first end;
      (ii) a flexible, compressible tube means for conveying a fluid therethrough and extending between said first and second ends of said back-up member and abutting said back-up member over a predetermined zone;
      (iii) an elongated, generally rigid tube extending outward of and supported by said tubular barrel;
      (iv) means for coupling said flexible, compressible tube in fluid communication with said generally rigid tube; and
   (b) a reusable, flow-control member including:
      (i) a housing having means for receiving and supporting said back-up member and said tubular barrel of said disposable cartridge said housing having at least one aperture through a predetermined surface thereof;
      (ii) lever means pivotally supported on a fulcrum within said housing, said lever means having a first end manually accessible through said aperture in said housing and a second end normally pressing said flexible, compressible tube means against said back-up member in said zone with sufficient force to pinch and occlude said flexible tube means; and (c) said disposable cartridge and said housing, when joined together, comprising a pistol grip for said rigid tube with said first end of said lever means acting as a trigger, squeezing of said trigger lifting said second end of said lever means so as to no longer pinch and fully occlude said flexible tube means.

2. The suction/irrigator surgical instrument as in claim 1 and means in said housing for releasably fastening said disposable cartridge to said housing.

3. The suction/irrigator surgical instrument as in claim 1 wherein said means for coupling said flexible tube means in fluid communication with said generally rigid tube comprises tubular stub means projecting radially from said tubular barrel, said stub having a lumen intersecting a lumen in said tubular barrel, said flexible tube means being attachable to said stub.

4. The suction/irrigator surgical instrument as in claim 1 and further including spring means for normally urging said second end of said lever means against said flexible tube means to pinch and occlude said flexible tube.

5. The suction/irrigator surgical instrument as in claim 4 wherein said lever means comprises a lever of the first class, with said spring means disposed between said housing and said second end of said lever, the length of the lever between said fulcrum and said spring means being less than the length of said lever between said fulcrum and said first end.

6. The suction/irrigator surgical instrument as in claim 1 wherein said rigid tube is formed from a member of the group including stainless steel and plastic and has an outer diameter sufficiently small to be insertable through a endoscopic cannula.

7. The suction/irrigation surgical instrument as in claim 1 wherein said pistol grip is ergonomically contoured to conform to a user's hand.

8. The suction/irrigator surgical instrument as in claim 1 wherein said flexible, compressible tube means includes a lumen extending the full length thereof, said flexible, compressible tube means being integrally molded with a transversely extending tubular sleeve member which has a lumen in fluid communication with said lumen of said flexible compressible tube means, said lumen of said sleeve member receiving a portion of said rigid tube therein.

9. A suction/irrigator surgical instrument comprising:

(a) a disposable cartridge including:
 (i) a back-up member having first and second ends with an integrally formed tubular barrel at said first end thereof;
 (ii) a pair of flexible, compressible tubes extending between said first and second ends of said back-up member and abutting said back-up member over a predetermined zone;
 (iii) an elongated, generally rigid tube extending outward of said tubular barrel;
 (iv) means for coupling said pair of flexible, compressible tubes in fluid communication with said generally rigid tube within said tubular barrel; and (b) a reusable, fluid-flow control member including:

(i) a housing having a recess therein for receiving said tubular barrel of said disposable cartridge, said housing having a pair of apertures through a predetermined surface thereof;
(ii) first and second lever means individually cooperating with said pair of compressible tubes, each lever means pivotally supported on an associated fulcrum within said housing, said first and second lever means each having a first end manually accessible through one of said pair of apertures formed in said housing and a second end normally pressing one of said pair of flexible, compressible tubes against said back-up member in said zone with sufficient force to pinch and occlude said flexible tubes;
(c) said disposable cartridge and said housing, when fastened together, comprising a pistol grip for said rigid tube with said first end of each of said lever means acting as a trigger, squeezing of either of said triggers lifting said second end of its lever means so as to no longer pinch and fully occlude the one of said pair of flexible, compressible tubes with which it cooperates.

10. The suction/irrigator surgical instrument as in claim 9 and further including means in said housing for releasably fastening said disposable cartridge to said housing with said tubular barrel in said recess.

11. The suction/irrigator surgical instrument as in claim 9 and further including spring means for normally urging said second ends of said pair of lever means against said pair of flexible compressible tubes to pinch and occlude said compressible tubes.

12. The suction/irrigation surgical instrument as in claim 11 wherein each of said pair of lever means comprises a lever of the first class with said spring means disposed between said housing and said second end of said lever, the length of the lever between its said fulcrum and said spring means being less than the length of said lever between said pivotal support and said first end.

13. The suction/irrigation surgical instrument as in claim 9 wherein said rigid tube is formed from a member of the group including stainless steel and plastic and has an outer diameter sufficiently small to be insertable through the lumen of a laparoscopic cannula.

14. The suction/irrigation surgical instrument as in claim 9 wherein said pistol grip is ergonomically contoured to conform to a user's hand.

15. The suction/irrigator surgical instrument is in claim 9 wherein said pair of flexible, compressible tubes each includes a lumen extending the full length thereof, said pair of tubes being integrally molded with a transversely extending tubular sleeve member which has a lumen in fluid communication with the lumens of said pair of flexible, compressible tubes, said lumen of said tubular sleeve member receiving a portion of said rigid tube therein.

16. The suction/irrigator surgical instrument as in claim 15 wherein said sleeve member includes an elastomeric seal having an aperture through it, said seal being in coaxial alignment with said rigid tube.

17. The suction/irrigator surgical instrument as in claim 16 and further including a bore formed through said back-up member in longitudinal alignment with said sleeve member.

* * * * *